United States Patent
Okada et al.

(10) Patent No.: US 10,352,859 B2
(45) Date of Patent: *Jul. 16, 2019

(54) METHOD FOR DETERMINING QUANTITY OF BIOLOGICAL MATERIAL IN TISSUE SECTION

(71) Applicant: Konica Minolta, Inc., Tokyo (JP)

(72) Inventors: Fuminori Okada, Tokyo (JP); Takuji Aimiya, Nishitokyo (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

(*) Notice: Subject to any disclaimer, the term of this patent is extended or adjusted under 35 U.S.C. 154(b) by 578 days.

This patent is subject to a terminal disclaimer.

(21) Appl. No.: 15/024,216

(22) PCT Filed: Sep. 16, 2014

(86) PCT No.: PCT/JP2014/074420
§ 371 (c)(1),
(2) Date: Mar. 24, 2016

(87) PCT Pub. No.: WO2015/045962
PCT Pub. Date: Apr. 2, 2015

(65) Prior Publication Data
US 2016/0216209 A1    Jul. 28, 2016

(30) Foreign Application Priority Data
Sep. 26, 2013   (JP) ................... 2013-199782

(51) Int. Cl.
  G01N 21/64    (2006.01)
  G01N 33/50    (2006.01)
  G01N 33/569   (2006.01)

(52) U.S. Cl.
  CPC ..... G01N 21/6458 (2013.01); G01N 21/6428 (2013.01); G01N 33/5088 (2013.01); G01N 33/56966 (2013.01); G01N 2021/6439 (2013.01); G01N 2201/12 (2013.01); G01N 2333/70596 (2013.01)

(58) Field of Classification Search
  None
  See application file for complete search history.

(56) References Cited

U.S. PATENT DOCUMENTS

| | | | |
|---|---|---|---|
| 2008/0274202 A1 | 11/2008 | Kraig et al. | |
| 2013/0039848 A1* | 2/2013 | Bradbury | A61K 49/0019 424/1.37 |
| 2013/0157287 A1* | 6/2013 | Takanashi | G01N 21/6428 435/7.1 |
| 2015/0049936 A1 | 2/2015 | Tsunomori et al. | |

FOREIGN PATENT DOCUMENTS

| | | |
|---|---|---|
| EP | 2833123 A1 | 2/2015 |
| JP | 2008268167 A | 11/2008 |
| JP | 2013-057631 A | 3/2013 |
| JP | 2013088296 A | 5/2013 |
| WO | 2012029752 A1 | 3/2012 |

OTHER PUBLICATIONS

Notification of Reason for Rejection dated Mar. 6, 2018 from corresponding Japanese Patent Appiication No. 2015-539129 and English translation.
V. Tuominen, et al; ImmunoRatio-F: image analysis of Ki-67 using cytokeratin immunofluorescence correction; URL:http://mitel.dimi.uniud.it/tp2012/presentations/A8-Isola.pdf; 11th European Congress on Telepathology and 5th International Congress on Virtual Microscopy; 9 pages, (2012).
V. Tuominen, et al; ImmunoRatio: a publicly available web application for quantitative image analysis of estrogen receptor . . . ; Breast Cancer Research; 2010, 12; R56; 12 pages.
International Search Report dated Dec. 9, 2014 for PCT/JP2014/074420, (4 pages).
Written Opinion of the International Searching Authority in English and Japanese dated Dec. 9, 2014 for PCT/JP2014/074420, (8 pages).
Extended European Search Report dated Apr. 4, 2017 corresponding European Application No./Patent No. 14847697.1-1554 / 3040724 PCT/JP2014074420; Applicant: Konica Minolta Inc.; Total of 7 pages.
NPL reference No. XP001574240 by Rivan Say, et al, "Bioconjugated and Cross-Linked Bionanostructures for Bifunctional Immunohistochemical Labeling", Microscopy and Microanalysis,vol. 18, No. 2, Apr. 2012, pp. 324-330.

* cited by examiner

Primary Examiner — Bao Thuy L Nguyen
Assistant Examiner — Ellen J Marcsisin
(74) Attorney, Agent, or Firm — Lucas & Mercanti, LLP

(57) ABSTRACT

An object of the present invention is to provide a method of detecting a specific tissue or cell in a sample tissue section and accurately specifying both the position(s) and amount of a biological substance of interest that is expressed on the specific tissue or cell. The method of quantifying a biological substance in a tissue section according to the present invention comprises: (1) performing bright-field observable immunostaining that specifically stains a first biological substance in the tissue section (first immunostaining); (2) performing immunostaining with a fluorescent substance-containing nanoparticle that specifically stains a second biological substance in the tissue section (second immunostaining); (3) specifying the expression position(s) of the second biological substance in the tissue section by comparing the position of a stained image of the first immunostaining and the position of a stained image of the second immunostaining; and (4) determining the expression amount of the second biological substance by measuring the fluorescence intensity of the stained image of the second immunostaining.

12 Claims, 1 Drawing Sheet

[Fig. 1]
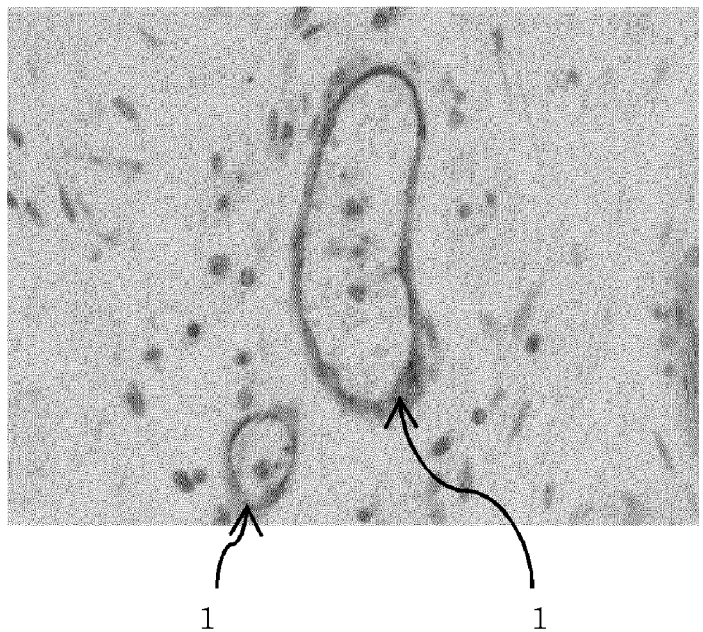
[Fig. 2]
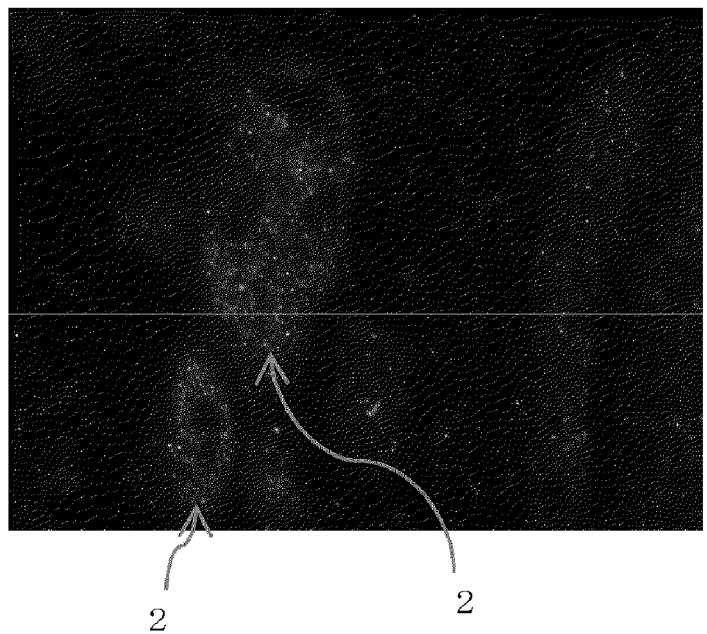

METHOD FOR DETERMINING QUANTITY OF BIOLOGICAL MATERIAL IN TISSUE SECTION

CROSS REFERENCE TO RELATED APPLICATION

This Application is a 371 of PCT/JP2014/074420 filed on Sep. 16, 2014 which, in turn, claimed the priority of Japanese Patent Application No. JP2013-199782 filed on Sep. 26, 2013, both applications are incorporated herein by reference.

TECHNICAL FIELD

The present invention relates to a method of quantifying a biological substance in a tissue section. More particularly, the present invention relates to a method of quantifying a biological substance in a tissue section using immunostaining.

BACKGROUND ART

In the field of pathological diagnosis, it is useful to detect a specific cell(s) or tissue from a specimen of a sampled tissue section and quantify the expression level of a substance associated with a lesion on the specific cell(s) or tissue, and methods utilizing immunohistochemistry have been examined for this purpose.

Immunohistochemistry (IHC) is widely known as a histological (histochemical) technique for detecting an antigen in a tissue sample using an antibody. This immunohistochemistry is sometimes referred to as "immunostaining" or the like (hereinafter, the term "immunohistochemical staining" may also be used for immunohistochemistry) because it involves a color-developing operation in order to visualize an antigen-antibody reaction that is intrinsically invisible. Due to this characteristic feature of visualizing the location of an antigen-antibody reaction, immunohistochemistry is widely used in the fields of medicine and life chemistry for the purpose of detecting the location of a biological substance in a tissue sample.

In IHC, as a method of visualizing the location of an antigen-antibody reaction, a staining method that can be observed in a bright field is widely used and, specifically, a technique using a substrate that is converted into a pigmentary substance by an enzyme is commonly used. For example, in clinical scenes, it is widely performed to stain and thus visualize an antibody bound to an antigen of interest in a tissue sample using peroxidase (POD) and diaminobenzidine (DAB) and to detect the expression amount of the specific antigen by bright-field observation through the thus visualized antibody. This bright-field observation is advantageous in that, as compared to the below-described method using a light-emitting substance, more detailed information on a target molecule can be obtained by comprehensively judging the information obtained in an analog manner such as staining color. As a method of distinguishing cytoma and specifying the position of the cytoma in a specimen using such immunostaining, an immunostaining technology which uses a marker specifically expressed in cells as a target has been generally employed.

As a method of evaluating the expression level of a biological substance of interest in a tissue section with high accuracy using immunohistochemistry, there is known a method which comprises performing immunostaining with a fluorescent substance-containing nanoparticle, detecting the thus generated fluorescent bright dots and then evaluating the expression level of a biological substance (Patent Document 1). In this method, the brightness distribution corresponding to the biological substance of interest can be measured by the use of the fluorescent substance-containing nanoparticle; however, it is difficult to specify the positional relationship between a specific tissue or cell in a tissue section and the biological substance of interest and thus to measure the brightness distribution by selecting the biological substance of interest expressed on the specific tissue or cell.

In addition, a method of simultaneously performing bright-field observable staining by an enzyme antibody method (DAB staining that uses an enzyme reaction) and fluorescent dye staining by a fluorescent antibody method (staining that uses a fluorescent dye) on a single tissue section has been reported (Non-patent Documents 1 and 2). In this method, although a biological substance of interest is quantified using a fluorescent dye, since a sufficient fluorescence intensity cannot be obtained at those spots where the biological substance is expressed in a small amount, it is difficult to quantify the biological substance of interest in some cases. For instance, in an example in which Ki-67-positive cells were stained by an enzyme antibody method and cytokeratin was fluorescently stained by a fluorescent antibody method, it is reported that there were cases where fluorescence observation of cytokeratin was difficult due to inadequate amount of fluorescence (Non-patent Document 2).

As a method of quantifying a protein by multiple fluorescent staining, there has also been proposed a method that comprises staining a protein of interest to be quantified and a reference protein with different fluorescent dye-labeled antibodies, measuring the total fluorescence intensities of the respective proteins and then quantifying the protein of interest based on the ratio of the thus measured total fluorescence intensities (Patent Document 2).

As described above, with regard to a method of detecting a specific tissue or cell in a sampled tissue section and quantifying a biological substance of interest that is expressed on the specific tissue or cell, there is a demand for a method of more accurately specifying both the expression position (s) and the expression amount.

PRIOR ART REFERENCES

Patent Documents

[Patent Document 1] JP-A-2013-088296
[Patent Document 2] JP-A-2008-268167

Non-Patent Documents

[Non-patent Document 1] Tuominen, V.; Ruotoisteumaki, S.; Viitanen, A.; Jumppanen, M. and Isola, J; Breast Cancer Research 2010, 12:R56, "ImmunoRatio-F: a publicly available web application for quantitative image analysis of estrogen receptor (ER), progesterone receptor (PR), and Ki-67"

[Non-patent Document 2] "URL: http://mitel.dimi.uniud.it/tp2012/presentations/A8-Isola.pdf" Vilppu Tuominen, Sofia Heinonen, Jorma Isola, "ImmunoRatio-F: image analysis of Ki-67 using cytokeratin immunofluorescence correction"

SUMMARY OF THE INVENTION

Problems to be Solved by the Invention

An object of the present invention is to provide a method of detecting a specific tissue or cell in a sampled tissue section and accurately specifying both the position(s) and amount of a biological substance of interest that is expressed on the specific tissue or cell.

Technical Solution

The present inventors discovered that, by staining a biological substance for specifying a specific tissue or cell (first biological substance) and a biological substance of interest for which the expression amount is quantified (second biological substance) by different methods in the same tissue section and comparing the positions of the stained images of these biological substances, the expression positions of the biological substance of interest (second biological substance) can be accurately specified; and that, by staining the biological substance of interest (second biological substance) with a fluorescent substance-containing nanoparticle, the biological substance of interest (second biological substance) can be accurately quantified even when the expression amount thereof is small, thereby completing the present invention.

That is, the present invention comprises the following items.

[1] A method of quantifying a biological substance in a tissue section, the method comprising:

(1) performing bright-field observable immunostaining that specifically stains a first biological substance in the tissue section (first immunostaining);

(2) performing immunostaining with a fluorescent substance-containing nanoparticle that specifically stains a second biological substance in the tissue section (second immunostaining);

(3) specifying the expression position(s) of the second biological substance in the tissue section by comparing the position of a stained image of the first immunostaining and position of a stained image of the second immunostaining; and (4) determining the expression amount of the second biological substance by measuring the fluorescence intensity of the stained image of the second immunostaining.

[2] The method according to [1], wherein the fluorescence intensity of the stained image of the second immunostaining is measured at a position(s) where the stained image of the first immunostaining and that of the second immunostaining overlap with each other.

[3] The method according to [1] or [2], wherein the first immunostaining and the second immunostaining are performed on the same tissue section.

Advantageous Effects of Invention

According to the present invention, a method of detecting a specific tissue or cell in a tissue section and accurately specifying both the position(s) and amount of a biological substance of interest that is expressed on the specific tissue or cell can be provided.

That is, by detecting a specific tissue or cell based on a stained image of a first biological substance that can be observed in a bright field and measuring the bright spots and the brightness distribution in a fluorescently stained image of a second biological substance for those parts where the position of the stained image of the first biological substance and the position of the fluorescently stained image (the number of bright spots and brightness distribution) of the second biological substance overlap with each other, the second biological substance (biological substance of interest) expressed on the specific tissue or cell can be selectively quantified. Further, since the second biological substance is stained with a fluorescent substance-containing nanoparticle, a high detection performance (sensitivity) can be attained even when the expression amount of the second biological substance is small.

BRIEF DESCRIPTION OF THE DRAWINGS

FIG. 1 shows a stained image obtained by the bright-field observable immunostaining performed in Example 2 of the present invention (tissue section: human liver tissue, immunostaining: CD31 antibody, dye: DAB).

FIG. 2 shows a stained image obtained by the immunostaining with a fluorescent substance-containing nanoparticle that was performed in Example 2 of the present invention (tissue section: the same human liver tissue as shown in FIG. 1, immunostaining: VEGFR2 antibody, dye: SulfoRhodamine 101-containing nanoparticle).

MODE FOR CARRYING OUT THE INVENTION

The mode for carrying out of the present invention will now be described in detail; however, the present invention is not restricted thereto.

1. Substance to be Detected and Substance to be Quantified

The present invention is a method of detecting a specific tissue or cell (hereinafter, referred to as "detection subject") in a sampled tissue section and accurately specifying both the position(s) and amount of a biological substance of interest (hereinafter, referred to as "substance to be quantified") that is expressed on the detection subject. In the present invention, a combination of the subject tissue section, detection subject and substance to be quantified can be selected in accordance with the examination purpose. For example, quantification of VEGFR-1, VEGFR-2, VEGFR-3 or the like expressed on vascular endothelial cells in a liver tissue section, quantification of VEGFR-1, VEGFR-2, VEGFR-3 or the like expressed on lymphatic endothelial cells in an esophageal tissue section, or quantification of Ki67 expressed on epithelial cells in a breast tissue section can be performed.

2. Tissue Section

The tissue section in the present invention is not particularly restricted as long as it is a section to which an immunostaining method can be applied, and such a tissue section can be prepared by a known method. For example, a paraffin-embedded section or the like that is widely used as a pathological section can be used as the tissue section.

3. Immunostaining

In the present invention, bright-field observable immunostaining that specifically stains a first biological substance in a tissue section (first immunostaining) and immunostaining with a fluorescent substance-containing nanoparticle that specifically stains a second biological substance in the tissue section (second immunostaining) are performed. In other words, the detection subject is detected based on a stained image obtained by the first immunostaining and the substance to be quantified is quantified based on the bright spots and the brightness distribution of a fluorescently stained image obtained by the second immunostaining.

In this case, these immunostainings are each performed using a "labeled probe" in which an antibody that specifically binds to the first or second biological substance (hereinafter, referred to as "target substance") and a visualizable substance (hereinafter, referred to as "label") are bound with each other. In other words, in the labeled probe, an antibody to a target substance is bound with a label. Here, the method of binding the antibody and the label is not particularly restricted and, in addition to a case where they are directly bound with each other, the present invention also encompasses those cases where the antibody and the label are bound through a secondary antibody.

Hereinafter, a labeled probe for performing the first immunostaining is referred to as "the first labeled probe", and a labeled probe for performing the second immunostaining is referred to as "the second labeled probe".

In the present invention, it is required that the first labeled probe and the second labeled probe do not inhibit each other's antigen-antibody reaction with their respective target substance.

(1) First Labeled Probe
(a) First Biological Substance

The first biological substance is a target substance of immunostaining (the first immunostaining) contained in the detection subject. As the first biological substance, a substance which functions as an antigen on the tissue or cell that is the detection subject may be selected so that bright-field observable staining is performed on the detection subject to such an extent that conforms to the examination purpose. For example, the first biological substance may be CD31, CD34 or the like for immunostaining of vascular endothelial cells, podoplanin or the like for immunostaining of lymphatic endothelial cells, or cytokeratin or the like for immunostaining of epithelial cells.

(b) Antibody Binding to First Biological Substance

An antibody that specifically binds to the first biological substance can be obtained by an ordinary method.

(c) Label

A label is used for visualizing a labeled probe bound to a target substance on a tissue section, and the label contained in the first labeled probe is a label for performing bright-field observable staining.

In the present invention, the term "bright-field observable staining" refers to staining that is directly visualized in a form visible under an ordinary light microscope (in other words, staining that reflects visible light) without excitation by an energy applied from outside. The phrase "directly visualized in a form visible" refers to achieving a state where the site(s) of specific binding reaction between a target substance and a probe can be directly observed without performing any secondary operation such as development.

Examples of such a label contained in the first labeled probe are as follows.

(Pigmentation-inducing Label)

Examples of a label that enables bright-field observation of the present invention include substances that induce pigmentation (pigmentation-inducing labels), in other words, enzymes that modify a substrate to cause the generation of a pigmentary chemical species. Examples of such enzymes include peroxidases such as horseradish peroxidase (HRP) and other enzymes such as alkaline phosphatase (ALP) and glucosidase.

(Substrate Used for Pigmentation)

As a substrate to be converted into a pigmentary substance by an enzyme as described above, a substrate that is commonly used as a chromogenic substrate in conventionally known assays based on a chromogenic substrate conversion method can be used. Examples of such a substrate include, but not limited to, substrates for oxidoreductases such as a substrate for horseradish peroxidase (HRP), substrates for phosphatases such as a substrate for alkaline phosphatase (ALP), and substrates for glycosidases such as a substrate for β-galactosidase.

Specific examples of a substrate used for an enzyme reaction by HRP include 3,3'-diaminobenzidine (DAB), 3-p-hydroxyphenylpropionic acid (HPPA), ECL plus (trademark) and 4-chloro-1-naphthol/4-chloronaphthalen-1-ol. Thereamong, DAB is preferably used because it is widely used from the standpoints of its color difference from hematoxylin (blue), which is commonly used for nuclear staining, and storage stability.

Examples of a substrate used for an enzyme reaction by alkaline phosphatase (ALP) include a 5-bromo-4-chloro-3-indolyl phosphate/nitroblue tetrazolium salt (BCIP/NBT), 4-methylumbelliferyl phosphate (MUP), 6,8-difluoro-4-methylumbelliferyl phosphate (DiFMUP), AttoPhos (registered trademark), and 9H-(1,3-dichloro-9,9-dimethylacridin-2-one-7-yl)phosphate (DDAOP).

Examples of a substrate used for an enzyme reaction by β-galactosidase include 5-bromo-4-chloro-3-indolyl-β-D-galactopyranoside (X-gal), 9H-(1,3-dichloro-9,9-dimethyl-acridin-2-one-7-yl)-β-D-galactop yranoside (DDAOG), and 4-methylumbelliferyl-β-D-galactoside (MUG).

(d) First Labeled Probe

The first labeled probe can be obtained by binding the above-described antibody that binds to the first biological substance with the above-described label. In this case, the method of binding the antibody and the label is not particularly restricted and, as described above, in addition to a case where they are directly bound with each other, the present invention also encompasses those cases where the antibody and the label are bound through a secondary antibody.

Such binding of the antibody and the label can be achieved by binding the label to the antibody in accordance with a commonly used method. Examples of a specific labeling method include a method of labeling the antibody through an antibody (secondary antibody) having a specific affinity for the antibody; a biotin-avidin method; a method that utilizes the coupling reaction between a thiol group and a maleimide group; a method that uses an existing chemical linker; a cross-linking reaction method that uses a cross-linking agent (such as 1-ethyl-3-(3-dimethylaminopropyl) carbodiimide (EDC)); and an ionic bond method (see the below-described Examples).

(2) Second Labeled Probe
(a) Second Biological Substance

The second biological substance is a target substance of immunostaining (the second immunostaining) contained in the substance to be quantified. A substance which functions as an antigen on the substance to be quantified can be selected so that quantification that conforms to the examination purpose is performed. However, the substance to be quantified is generally a protein and, in that case, the substance to be quantified itself is the second biological substance. Examples of the second biological substance include vascular endothelial growth factor receptors (VEGFR-1, VEGFR-2 and VEGFR-3) and cell growth-related proteins such as Ki-67.

(b) Antibody Binding to Second Biological Substance

An antibody that specifically binds to the second biological substance can be obtained by an ordinary method.

(c) Label

A label is used for visualizing a labeled probe bound to a target substance on a tissue section, and the label contained in the second labeled probe is a fluorescent substance-containing nanoparticle.

The term "fluorescent substance-containing nanoparticle" refers to a nano-sized particle having a structure in which two or more (two or more molecules) of a fluorescent substances are contained in a particle (matrix) made of an organic or inorganic material. In the present invention, the fluorescent substance is a fluorescent dye or a fluorescent nanoparticle, and examples thereof include fluorescent dye-containing nanoparticles and fluorescent nanoparticle-containing nanoparticles. The fluorescent substance-containing nanoparticle (fluorescent dye-containing nanoparticle or fluorescent nanoparticle-containing nanoparticle) used in the present invention can be prepared by a known method by selecting, in accordance with the intended purpose thereof, a fluorescent dye or fluorescent nanoparticle used as a fluorescent substance and a particle-forming organic or inorganic material as raw materials.

Examples of the particle-forming organic or inorganic material include those which are capable of stably containing a fluorescent substance, such as polystyrene, polyamide, polylactic acid, polyacrylonitrile, polyglycidyl methacrylate, polymelamine, polyurea, polybenzoguanamine, polyfuran, polyxylene, phenol resins, polysaccharides and silica. When a fluorescent substance is incorporated into such a particle, deterioration thereof caused by irradiation with an excitation light is less likely to occur (superior light resistance is attained) as compared to a case where a fluorescent dye is used by itself and, by incorporating plural fluorescent substances in one particle, the fluorescence intensity (brightness) of the light emitted from one particle can be increased.

(Fluorescent Dye-containing Nanoparticle)

The fluorescent dye-containing nanoparticle contains two or more fluorescent dye molecules in one particle described above. The fluorescent dye to be contained is not particularly restricted and can be selected in accordance with the intended excitation light, fluorescence wavelength and the like.

The fluorescent dye to be contained can be selected from, for example, rhodamine-based dye molecules, squarylium-based dye molecules, cyanine-based dye molecules, aromatic ring-based dye molecules, oxazine-based dye molecules, carbopyronine-based dye molecules and pyrromethene-based dye molecules. Alternatively, the fluorescent dye to be contained can also be selected from, for example, Alexa Fluor (registered trademark, manufactured by Invitrogen)-based dye molecules, BODIPY (registered trademark, manufactured by Invitrogen)-based dye molecules, Cy (registered trademark, manufactured by GE Healthcare)-based dye molecules, DY (registered trademark, Dyomics GmbH)-based dye molecules, HiLyte (registered trademark, manufactured by AnaSpec Inc.)-based dye molecules, DyLight (registered trademark, manufactured by Thermo Fisher Scientific K.K.)-based dye molecules, ATTO (registered trademark, manufactured by ATTO-TEC GmbH)-based dye molecules and MFP (registered trademark, manufactured by Mobitec Co., Ltd.)-based dye molecules. The generic names of these dye molecules are designated based on the main structure (skeleton) or registered trademark of the respective compounds; therefore, those of ordinary skill in the art can properly understand the scope of the fluorescent dyes belonging to the respective generic names without having to bear undue trial and error.

Specific examples of the rhodamine-based dye molecules include 5-carboxy-rhodamine, Texas Red and SulfoRhodamine 101. Specific examples of the squarylium-based dye molecules include SRfluor 680-carboxylate. Specific examples of the cyanine-based dye molecules include 1-butyl-2-[5-(1-butyl-1,3-dihydro-3,3-dimethyl-2H-indol-2-ylidene)-penta-1,3-dienyl]-3,3-dimethyl-3H-indolium hexafluorophosphate. Specific examples of the aromatic ring-based dye molecules include N,N-bis-(2,6-diisopropylphenyl)-1,6,7,12-(4-tert-butylphenoxy)-perylen-3,4,9,10-tetracarbonacid diimide. Specific examples of the oxazine-based dye molecules include Cresyl violet. Specific examples of the carbopyronine-based dye molecules include CARBOPYRONIN 149. Specific examples of the pyrromethene-based dye molecules include PYRROMETHENE 650.

Further, specific examples of the Alexa Fluor-based dye molecules include Alexa Fluor 555 (manufactured by Invitrogen). Specific examples of the BODIPY-based dye molecules include BODIPY FL (manufactured by Invitrogen). Specific examples of the Cy-based dye molecules include Cy 3.5 (manufactured by GE Healthcare). Specific examples of the DY-based dye molecules include DY-590 (manufactured by Dyomics GmbH). Specific examples of the HiLyte-based dye molecules include HiLyte 594 (manufactured by AnaSpec Inc.). Specific examples of the DyLight-based dye molecules include DyLight 594 (manufactured by Thermo Fisher Scientific K.K.). Specific examples of the ATTO-based dye molecules include ATTO 590 (manufactured by ATTO-TEC GmbH). Specific examples of the MFP-based dye molecules include MFP 590 (manufactured by Mobitec Co., Ltd.).

Examples of other dyes include C-phycocyanin, phycocyanin, APC (allophycocyanin), APC-XL and Northern-Lights 637 (all of which are manufactured by R&D Systems, Inc.).

Further, specific examples of the fluorescent dye also include derivatives of the above-described dyes (which can function as a fluorescent dye, such as known derivatives).

The method of producing the fluorescent dye-containing nanoparticle is not particularly restricted, and the fluorescent dye-containing nanoparticle is produced by a commonly used method. Examples thereof include a method in which, after binding a fluorescent dye molecule (s) to a resin monomer used as a particle raw material, a particle is synthesized by polymerizing the resin monomer; and a method of introducing a fluorescent dye(s) to a polymerized resin particle through adsorption or binding; a method in which a resin monomer and a fluorescent dye(s) are mixed and then polymerization of the resin monomer and binding of the fluorescent dye(s) are performed simultaneously. In the fluorescent dye-containing nanoparticles produced by these methods, plural fluorescent dye molecules are usually contained in one particle.

The average particle size of the fluorescent dye-containing nanoparticle is not particularly restricted; however, it is usually 10 to 500 nm, preferably 50 to 200 nm. Further, the variation coefficient which indicates the variation in the particle size is also not particularly restricted; however, it is usually 20% or less, preferably 5 to 15%.

It is noted here that the particle size of a fluorescent dye-containing nanoparticle can be determined by taking an electron micrograph thereof using a scanning electron microscope (SEM), measuring the cross-sectional area of the fluorescent dye-containing nanoparticle and then determining the particle size as the diameter of a circular area corresponding to the measured value (area-equivalent circle diameter). With regard to the average particle size (average particle diameter) and the variation coefficient of a group of fluorescent dye-containing nanoparticles, after measuring the particle size (particle diameter) for a sufficient number (for example, 1,000) of the fluorescent dye-containing nanoparticles in the above-described manner, the average particle size is calculated as the arithmetic mean of the measured values and the variation coefficient is calculated by the following equation: 100×(standard deviation of particle size)/(average particle size).

(Fluorescent Nanoparticle-containing Particle)

The fluorescent nanoparticle-containing particle contains two or more fluorescent nanoparticles in one particle described above. The fluorescent nanoparticles to be contained are not particularly restricted and can be selected in accordance with the intended excitation light, fluorescence wavelength and the like.

The fluorescent nanoparticles to be contained have a particle size of 1 to 500 nm, preferably 10 to 200 nm. These fluorescent nanoparticles are composed of a semiconductor or fluorophore. As the semiconductor, for example, a group II-VI semiconductor such as ZnSe, ZnTe, CdSe, CdTe, PbS, PbSe or PbTe, or a group III-V semiconductor such as AlAs, AlSb, GaP, GaAs, GaSb, InP, InAs or InSb can be used. From the standpoint of toxicity, GaP or InP can be suitably used. In the fluorophore, for example, $Y_2O_3$, $YVO_4$, ZnO or ZnS can be used as the matrix and Eu or Nd can be used as the emission center. An excitation wavelength suitable for observation is set by adjusting the particle size, matrix composition and impurity amount of the fluorescent nanoparticles.

The method of producing the fluorescent nanoparticle-containing nanoparticle by incorporating such fluorescent nanoparticles into the above-described particle is not particularly restricted, and the fluorescent nanoparticle-containing nanoparticle is produced by a commonly used method. Examples thereof include a method in which, after binding fluorescent nanoparticles to a resin monomer used as a particle raw material, a particle is synthesized by polymerizing the resin monomer; a method of introducing fluorescent nanoparticles to a polymerized resin particle through adsorption or binding; and a method in which a resin monomer and fluorescent nanoparticles are mixed and then polymerization of the resin monomer and binding of the fluorescent nanoparticles are performed simultaneously. In the fluorescent nanoparticle-containing nanoparticles produced by these methods, plural fluorescent nanoparticles are usually contained in one particle. An excitation wavelength suitable for observation is set by adjusting the particle size, matrix composition and impurity amount of the contained fluorescent nanoparticles. The fluorescent nanoparticle-containing particle has a particle size of 10 to 500 nm, preferably 50 to 200 nm.

The particle size of a fluorescent nanoparticle-containing nanoparticle can be determined in the same manner as in the case of the above-described fluorescent dye-containing nanoparticle.

(d) Second Labeled Probe

The second labeled probe can be obtained by binding the above-described antibody that binds to the second biological substance with the above-described label. In this case, the method of binding the antibody and the label is not particularly restricted and, as described above, in addition to a case where they are directly bound with each other, the present invention also encompasses those cases where the antibody and the label are bound through a secondary antibody.

Such binding of the antibody and the label can be achieved by binding the label to the antibody in accordance with a commonly used method. Examples of a specific labeling method include a method of labeling the antibody through an antibody (secondary antibody) having a specific affinity for the antibody; a biotin-avidin method; a method that utilizes the coupling reaction between a thiol group and a maleimide group; a method that uses an existing chemical linker; a cross-linking reaction method that uses a cross-linking agent (such as 1-ethyl-3-(3-dimethylaminopropyl) carbodiimide (EDC)); and an ionic bond method (see the below-described Examples).

(3) Immunostaining

In the present invention, the above-described first immunostaining and second immunostaining are performed on a tissue section. In this case, it is preferred that both of these immunostainings be performed on the same tissue section so as to specify the position(s) at which the substance to be quantified is expressed on the detection subject by comparing the positional relationship between the stained images obtained by the respective immunostainings; however, it is also possible to perform each immunostaining on adjacent tissue sections that are obtained in the process of cutting out sections.

These immunostainings can each be performed by a commonly used method.

4. Comparisons of Positions of Stained Images

In the present invention, the positions of the second biological substance expressed on a tissue section are specified by comparing the position of a stained image of the first immunostaining and the position of a stained image of the second immunostaining. It is noted here that, as described above, the stained image of the first immunostaining can be observed in a bright field and the stained image of the second immunostaining is a fluorescently stained image. Accordingly, the stained image of the first immunostaining is observed under a light microscope, while the stained image of the second immunostaining is observed under a fluorescence microscope. For the positional comparison between these stained images, any method can be employed with no particular restriction as long as the method is capable of determining to which positions on the stained image of the first immunostaining the bright spots and brightness distribution obtained by the second immunostaining correspond. For example, by loading the stained image of the first immunostaining and the stained image of the second immunostaining to a computer and comparing the positional relationships between these images, the positional relationships of the bright spots and brightness distribution obtained by the second immunostaining with respect to the stained image of the first immunostaining can be judged. Examples of an analysis software for such process include a commercially available image analysis software, ImageJ.

Since the detection subject on a tissue section is specified by the first immunostaining, as long as the positional relationships between the above-described stained images can be determined by positional comparison, the bright spots and brightness distribution obtained by the immunostaining of the substance to be quantified (second biological substance) that is expressed on the detection subject in the tissue section can be specified. In other words, the bright spots and brightness distribution of the second immunostaining that are found at the positions at which the stained image of the first immunostaining and that of the second immunostaining overlap with each other are the bright spots and brightness distribution of the substance to be quantified (second biological substance) that is expressed on the detection subject.

5. Determination of Expression Amount of Substance to be Quantified (Second Biological Substance)

The amount of the substance to be quantified (second biological substance) that is expressed on the detection subject is determined by measuring the fluorescence intensity of the thus specified stained image of the second immunostaining. In this case, "measuring the fluorescence intensity" refers to measuring the number of bright spots or the fluorescence brightness for the thus specified bright spots or brightness distribution.

The number of bright spots and the fluorescence brightness can be measured by a commonly used method. For example, the number of bright spots or the fluorescence brightness is measured by loading the stained image of the second immunostaining to a computer and performing image processing by an arithmetic means using an analysis software for the specified bright spots or brightness distribution. Examples of the analysis software include "ImageJ", which is a commercially available image analysis software, and "G-Count", which is an automatic total bright spot measuring software manufactured by G-Angstrom K.K.

By comparing the thus measured number of bright spots or fluorescence brightness between samples or between a sample and a reference sample, the amount of the substance to be quantified that is expressed on the detection subject in a sampled tissue section can be determined.

EXAMPLES

The present invention will now be described more concretely by way of examples thereof; however, the scope of the present invention is not restricted thereto.

Example 1

(1) Bright-field Observable Immunostaining on First Biological Substance (First Immunostaining)

After immersing a liver tissue slide (T032a, manufactured by Biomax, Inc.) in xylene to remove paraffin, the liver tissue slide was autoclaved in a citrate buffer (pH 6.0) for 15 minutes. Then, the slide was washed with PBS, and 10% rabbit serum (manufactured by Nichirei Corporation) was added thereto. The resulting slide was left to stand at room temperature for 1 hour.

After washing this slide with PBS, an anti-CD31 antibody (mouse antibody, manufactured by Abcam plc.) was added thereto, and the slide was left to stand at room temperature for 30 minutes. The slide was again washed with PBS and, after adding thereto a dextran polymer peroxidase-labeled anti-mouse antibody (manufactured by Nichirei Corporation), the slide was left to stand at room temperature for 30 minutes. Using a DAB substrate kit (manufactured by Nichirei Corporation), the slide was immunostained with an enzyme and diaminobenzidine (DAB) as a chromogenic substrate, followed by washing with PBS.

The slide was sequentially immersed in ethanol and xylene and, after adding thereto a mounting medium (Entellan New, manufactured by Merck KGaA), a cover glass was placed on the slide to prepare an evaluation slide.

(2) Immunostaining on Second Biological Substance with Fluorescent Dye-containing Nanoparticle (Second Immunostaining)

(a) Preparation of Antibody-bound Fluorescent Melamine Resin Particle (Average Particle Size: 150 nm)

After adding and dissolving 14.4 mg SulfoRhodamine 101 (manufactured by Sigma-Aldrich) in 22 mL of water, 2 mL of 5% aqueous solution of EMULGEN 430 (manufactured by Kao Corporation), was added. The resulting solution was heated to 70° C. with stirring on a hot stirrer, and 0.65 g of a melamine resin material, NIKALAC MX-035 (manufactured by Nippon Carbide Industries Co., Ltd.), was added thereto. Then, 680 µL of 10% aqueous solution of dodecylbenzenesulfonic acid (manufactured by Kanto Chemical Co., Inc.) was further added, and the resulting solution was heated with stirring at 70° C. for 50 minutes. Thereafter, this solution was further heated with stirring at 90° C. for 20 minutes. The resulting particle-containing solution was washed with pure water so as to remove impurities such as excess resin material and dye. This solution was centrifuged at 20,000 G for 15 minutes using a centrifugal machine (micro-refrigerated centrifuge 3740, manufactured by Kubota Corporation) and, after removing the resulting supernatant, the precipitates were re-dispersed in ultrapure water by ultrasonication. The centrifugation, the removal of supernatant and the re-dispersion in ultrapure water were repeated five times.

Then, 0.1 mg of the thus obtained particles were dispersed in 1.5 mL of EtOH, and 2 µL of aminopropyltrimethoxysilane, LS-3150 (manufactured by Shin-Etsu Chemical Co., Ltd.), was added thereto. The resulting mixture was allowed to react for 8 hours to perform a surface amination treatment.

The thus obtained dye-containing nanoparticles were adjusted with PBS (phosphate-buffered physiological saline) containing 2 mM of EDTA (ethylenediamine tetraacetic acid) to a concentration of 3 nM. This solution was mixed with SM(PEG)12 (succinimidyl-[(N-maleomidopropionamid)-dodecaethylene glycol]ester, manufactured by Thermo Fisher Scientific K.K.) to a final concentration of 10 mM and allowed to react for 1 hour. The resulting mixture was centrifuged at 10,000 G for 20 minutes and the resulting supernatant was removed. Then, PBS containing 2 mM of EDTA was added to disperse the precipitates, and the resulting dispersion was centrifuged again. The precipitates were washed three times by the same procedure to obtain fluorescent dye-containing particles having a maleimide group at a terminal.

Meanwhile, streptavidin (manufactured by Wako Pure Chemical Industries, Ltd.) was subjected to a thiol group addition treatment with N-succinimidyl-S-acetylthioacetate (SATA), and the resultant was filtered through a gel-filtration column to obtain a solution of streptavidin capable of binding to dye-containing nanoparticles.

The above-described fluorescent nanoparticles and streptavidin were mixed in PBS containing 2 mM of EDTA and allowed to react for 1 hour. Then, the reaction was terminated with an addition of 10 mM mercaptoethanol. After concentrating the resulting solution using a centrifugation filter, unreacted streptavidin and the like were removed using a purification gel-filtration column, thereby obtaining streptavidin-bound SulfoRhodamine 101 dye-containing melamine nanoparticles.

(b) Preparation of Pathological Stain Solution

The thus obtained streptavidin-bound SulfoRhodamine 101 dye-containing melamine nanoparticles (average particle size: 150 nm) were added to PBS at a concentration of 0.06 nM to prepare a pathological stain solution.

(c) Immunostaining

A liver tissue slide of a tissue section adjacent to the tissue section of the above-described liver tissue slide of (1) was immersed in xylene to remove paraffin, and this liver tissue slide was subsequently autoclaved in a citrate buffer (pH 6.0) for 15 minutes. Then, the slide was washed with PBS, 10% goat serum (manufactured by Nichirei Corporation) was added thereto, and the resulting slide was left to stand at room temperature for 1 hour. After washing this slide with PBS, an anti-VEGFR-2 antibody (rabbit antibody, manufactured by Abcam plc.) was added thereto, and the slide was left to stand at room temperature for 30 minutes. The slide was again washed with PBS and, after adding thereto a biotin-labeled anti-rabbit antibody (manufactured by Nichirei Corporation), the slide was left to stand at room temperature for 30 minutes. To this slide, the above-prepared pathological stain solution was added after dilution and allowed to react at room temperature for 2 hours, and the slide was subsequently washed with PBS.

The slide was sequentially immersed in ethanol and xylene and, after adding thereto a mounting medium (Entellan New, manufactured by Merck KGaA), a cover glass was placed on the slide to prepare an evaluation slide.

(3) Evaluation of Stained Images

For the thus prepared evaluation slides, a stained image of the first immunostaining was obtained under a light microscope (manufactured by Carl Zeiss AG) and a fluorescently stained image of the second immunostaining was obtained under a fluorescence microscope (manufactured by Carl Zeiss AG), respectively. In the acquisition of the fluorescently stained image, the excitation wavelength was 575 to 600 nm and the fluorescence wavelength was 612 to 682 nm.

The thus obtained stained image of the first immunostaining and fluorescently stained image of the second immunostaining were evaluated. The results thereof are shown in Table 1-1.

Example 2

An evaluation slide was prepared in the same manner as in Example 1 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 3

Evaluation slides were prepared in the same manner as in Example 1 except that the first immunostaining was performed using an anti-CD34 antibody (mouse antibody, manufactured by Nichirei Corporation), and the thus obtained stained image of the first immunostaining and fluorescently stained image of the second immunostaining were evaluated. The results thereof are shown in Table 1-1.

Example 4

An evaluation slide was prepared in the same manner as in Example 3 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 5

Evaluation slides were prepared in the same manner as in Example 1 except that the second immunostaining was performed using an anti-VEGFR-1 antibody (rabbit antibody, manufactured by Abcam plc.), and the thus obtained stained image of the first immunostaining and fluorescently stained image of the second immunostaining were evaluated. The results thereof are shown in Table 1-1.

Example 6

An evaluation slide was prepared in the same manner as in Example 5 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 7

Evaluation slides were prepared in the same manner as in Example 3 except that the second immunostaining was performed using an anti-VEGFR-1 antibody (rabbit antibody, manufactured by Abcam plc.), and the thus obtained stained image of the first immunostaining and fluorescently stained image of the second immunostaining were evaluated. The results thereof are shown in Table 1-1.

Example 8

An evaluation slide was prepared in the same manner as in Example 7 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 9

Evaluation slides were prepared in the same manner as in Example 1 except that the first immunostaining was performed using an anti-podoplanin antibody (mouse antibody, manufactured by Medical & Biological Laboratories Co., Ltd.) and the second immunostaining was performed using an anti-VEGFR-1 antibody (rabbit antibody, manufactured by Abcam plc.), and the thus obtained stained image of the first immunostaining and fluorescently stained image of the second immunostaining were evaluated. The results thereof are shown in Table 1-1.

Example 10

An evaluation slide was prepared in the same manner as in Example 9 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 11

Evaluation slides were prepared in the same manner as in Example 1 except that the first immunostaining was performed using an anti-cytokeratin AE1/AE3 antibody (mouse antibody, manufactured by Dako Co., Ltd.) and the second immunostaining was performed using an anti-Ki67 antibody (rabbit antibody, manufactured by Nichirei Corporation), and the thus obtained stained image of the first immunostaining and fluorescently stained image of the second immunostaining were evaluated. The results thereof are shown in Table 1-1.

Example 12

An evaluation slide was prepared in the same manner as in Example 11 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 13

Evaluation slides were prepared in the same manner as in Example 11 except that the second immunostaining was performed using an anti-ER antibody (rabbit antibody, manufactured by Nichirei Corporation), and the thus obtained stained image of the first immunostaining and fluorescently stained image of the second immunostaining were evaluated. The results thereof are shown in Table 1-1.

Example 14

An evaluation slide was prepared in the same manner as in Example 13 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 15

Evaluation slides were prepared in the same manner as in Example 11 except that the second immunostaining was performed using an anti-PgR antibody (rabbit antibody, manufactured by Ventana Medical Systems, Inc.), and the thus obtained stained image of the first immunostaining and fluorescently stained image of the second immunostaining were evaluated. The results thereof are shown in Table 1-1.

Example 16

An evaluation slide was prepared in the same manner as in Example 15 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 17

Evaluation slides were prepared in the same manner as in Example 1 except that the first immunostaining was performed using an anti-CK7 antibody (mouse antibody, manufactured by Acris Antibodies GmbH), and the thus obtained stained image of the first immunostaining and fluorescently stained image of the second immunostaining were evaluated. The results thereof are shown in Table 1-1.

Example 18

An evaluation slide was prepared in the same manner as in Example 17 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 19

Evaluation slides were prepared in the same manner as in Example 17 except that the second immunostaining was performed using an anti-VEGFR-1 antibody (rabbit antibody, manufactured by Abcam plc.), and the thus obtained stained image of the first immunostaining and fluorescently stained image of the second immunostaining were evaluated. The results thereof are shown in Table 1-1.

Example 20

An evaluation slide was prepared in the same manner as in Example 19 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Example 21

Evaluation slides were prepared in the same manner as in Example 17 except that the second immunostaining was performed using an anti-VEGFR-3 antibody (rabbit antibody, manufactured by Abcam plc.), and the thus obtained stained image of the first immunostaining and fluorescently stained image of the second immunostaining were evaluated. The results thereof are shown in Table 1-1.

Example 22

An evaluation slide was prepared in the same manner as in Example 21 except that the second immunostaining was performed on the same liver tissue slide as the first immunostaining, and the thus obtained stained image of the first immunostaining and fluorescently stained image of the second immunostaining were evaluated. The results thereof are shown in Table 1-1.

Comparative Example 1

An evaluation slide was prepared by performing only the second immunostaining in Example 1 without the first immunostaining. The results of evaluating the thus obtained stained image are shown in Table 1-2.

Comparative Example 2

An evaluation slide was prepared in the same manner as in Example 2 except that the second immunostaining was performed using Streptavidin-Alexa Fluor (registered trademark) 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed in accordance with the product manual provided by Invitrogen. The thus obtained evaluation slide was evaluated. The results thereof are shown in Table 1-2.

Comparative Example 3

An evaluation slide was prepared by performing only the second immunostaining in Example 3 without the first immunostaining. The results of evaluating the thus obtained stained image are shown in Table 1-2.

Comparative Example 4

An evaluation slide was prepared in the same manner as in Example 4 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 5

An evaluation slide was prepared by performing only the second immunostaining in Example 5 without the first immunostaining. The results of evaluating the thus obtained stained image are shown in Table 1-2.

Comparative Example 6

An evaluation slide was prepared in the same manner as in Example 6 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 7

An evaluation slide was prepared by performing only the second immunostaining in Example 7 without the first immunostaining. The results of evaluating the thus obtained stained image are shown in Table 1-2.

Comparative Example 8

An evaluation slide was prepared in the same manner as in Example 8 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 9

An evaluation slide was prepared by performing only the second immunostaining in Example 9 without the first immunostaining. The results of evaluating the thus obtained stained image are shown in Table 1-2.

Comparative Example 10

An evaluation slide was prepared in the same manner as in Example 10 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 11

An evaluation slide was prepared by performing only the second immunostaining in Example 11 without the first immunostaining. The results of evaluating the thus obtained stained image are shown in Table 1-2.

Comparative Example 12

An evaluation slide was prepared in the same manner as in Example 12 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 13

An evaluation slide was prepared by performing only the second immunostaining in Example 13 without the first immunostaining. The results of evaluating the thus obtained stained image are shown in Table 1-2.

Comparative Example 14

An evaluation slide was prepared in the same manner as in Example 14 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 15

An evaluation slide was prepared by performing only the second immunostaining in Example 15 without the first immunostaining. The results of evaluating the thus obtained stained image are shown in Table 1-2.

Comparative Example 16

An evaluation slide was prepared in the same manner as in Example 16 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 17

An evaluation slide was prepared by performing only the second immunostaining in Example 17 without the first immunostaining. The results of evaluating the thus obtained stained image are shown in Table 1-2.

Comparative Example 18

An evaluation slide was prepared in the same manner as in Example 18 except that the second immunostaining was performed using Streptavidin-Alexa Fluor 594 conjugate (manufactured by Invitrogen) in place of the streptavidin-boundSulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 19

An evaluation slide was prepared by performing only the second immunostaining in Example 19 without the first immunostaining. The results of evaluating the thus obtained stained image are shown in Table 1-2.

Comparative Example 20

An evaluation slide was prepared in the same manner as in Example 20 except that the second immunostaining was performed using Streptavidin-Alexa Fluor 594 conjugate (manufactured by Invitrogen) in place of the streptavidin-bound SulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

Comparative Example 21

An evaluation slide was prepared by performing only the second immunostaining in Example 21 without the first immunostaining. The results of evaluating the thus obtained stained image are shown in Table 1-2.

Comparative Example 22

An evaluation slide was prepared in the same manner as in Example 22 except that the second immunostaining was performed using Streptavidin-Alexa Fluor 594 conjugate (manufactured by Invitrogen) in place of the streptavidin-boundSulfoRhodamine 101 dye-containing melamine nanoparticles. The second immunostaining using Streptavidin-Alexa Fluor 594 conjugate (manufactured by Invitrogen) was performed by the method described in Comparative Example 2. The thus obtained evaluation slide was evaluated. The results thereof are shown in Table 1-2.

[Evaluation Results of Evaluation Slides]

As shown in Table 1, even when the evaluation slides of different adjacent tissue sections were used, the expression positions of the second biological substance on the specific tissue or cells (the positions of the bright spots and the brightness distribution on the respective fluorescently stained images of the second immunostaining) were specified by comparing the stained image of the first immunostaining and the stained image of the second tissue section (Examples). Moreover, when the evaluation slides of the same tissue section were used, the expression positions of the second biological substance were easily and accurately specified without having to change slides (Examples). On the other hand, when the first immunostaining was not performed, it was difficult to specify the expression positions of the second biological substance on the specific tissue or cells (Comparative Examples).

Furthermore, with regard to the expression amount of the second biological substance (calculation of the number of bright spots and determination of the brightness distribution on the respective fluorescently stained images of the second immunostaining), when a fluorescent dye was used for the second immunostaining, the fluorescence intensity was low and it was thus difficult to determine the fluorescence brightness distribution (Comparative Examples); however, when fluorescent dye-containing nanoparticles were used, a sufficient fluorescence intensity was obtained and the fluorescence brightness distribution was thus determined with no problem (Examples).

TABLE 1-1

| | First immunostaining | Second immunostaining | Tissue section slide | Specification of expression positions of second biological substance (Note 1) | Determination of brightness distribution of second biological substance (Note 2) |
|---|---|---|---|---|---|
| Example 1 | CD31-DAB | VEGFR2-fluorescent dye-containing nanoparticle | adjacent | ○ | ◉ |
| Example 2 | CD31-DAB | VEGFR2-fluorescent dye-containing nanoparticle | same | ◉ | ◉ |
| Example 3 | CD34-DAB | VEGFR2-fluorescent dye-containing nanoparticle | adjacent | ○ | ◉ |
| Example 4 | CD34-DAB | VEGFR2-fluorescent dye-containing nanoparticle | same | ◉ | ◉ |
| Example 5 | CD31-DAB | VEGFR1-fluorescent dye-containing nanoparticle | adjacent | ○ | ◉ |
| Example 6 | CD31-DAB | VEGFR1-fluorescent dye-containing nanoparticle | same | ◉ | ◉ |
| Example 7 | CD34-DAB | VEGFR1-fluorescent dye-containing nanoparticle | adjacent | ○ | ◉ |

TABLE 1-1-continued

| | First immunostaining | Second immunostaining | Tissue section slide | Specification of expression positions of second biological substance (Note 1) | Determination of brightness distribution of second biological substance (Note 2) |
|---|---|---|---|---|---|
| Example 8 | CD34-DAB | VEGFR1-fluorescent dye-containing nanoparticle | same | ◉ | ◉ |
| Example 9 | Podoplanin-DAB | VEGFR3-fluorescent dye-containing nanoparticle | adjacent | ○ | ◉ |
| Example 10 | Podoplanin-DAB | VEGFR3-fluorescent dye-containing nanoparticle | same | ◉ | ◉ |
| Example 11 | Cytokeratin AE1/AE3-DAB | Ki67-fluorescent dye-containing nanoparticle | adjacent | ○ | ◉ |
| Example 12 | Cytokeratin AE1/AE3-DAB | Ki67-fluorescent dye-containing nanoparticle | same | ◉ | ◉ |
| Example 13 | Cytokeratin AE1/AE3-DAB | ER-fluorescent dye-containing nanoparticle | adjacent | ○ | ◉ |
| Example 14 | Cytokeratin AE1/AE3-DAB | ER-fluorescent dye-containing nanoparticle | same | ◉ | ◉ |
| Example 15 | Cytokeratin AE1/AE3-DAB | PgR-fluorescent dye-containing nanoparticle | adjacent | ○ | ◉ |
| Example 16 | Cytokeratin AE1/AE3-DAB | PgR-fluorescent dye-containing nanoparticle | same | ◉ | ◉ |
| Example 17 | CK7-DAB | VEGFR2-fluorescent dye-containing nanoparticle | adjacent | ○ | ◉ |
| Example 18 | CK7-DAB | VEGFR2-fluorescent dye-containing nanoparticle | same | ◉ | ◉ |
| Example 19 | CK7-DAB | VEGFR1-fluorescent dye-containing nanoparticle | adjacent | ○ | ◉ |
| Example 20 | CK7-DAB | VEGFR1-fluorescent dye-containing nanoparticle | same | ◉ | ◉ |
| Example 21 | CK7-DAB | VEGFR3-fluorescent dye-containing nanoparticle | adjacent | ○ | ◉ |
| Example 22 | CK7-DAB | VEGFR3-fluorescent dye-containing nanoparticle | same | ◉ | ◉ |

TABLE 1-2

| | First immunostaining | Second immunostaining | Tissue section slide | Specification of expression positions of second biological substance (Note 1) | Determination of brightness distribution of second biological substance (Note 2) |
|---|---|---|---|---|---|
| Comparative Example 1 | none | VEGFR2-fluorescent dye-containing nanoparticle | — | X | ○ |
| Comparative Example 2 | CD31-DAB | VEGFR2-fluorescent dye | same | ◉ | X |
| Comparative Example 3 | none | VEGFR2-fluorescent dye-containing nanoparticle | — | X | ○ |
| Comparative Example 4 | CD34-DAB | VEGFR2-fluorescent dye | same | ◉ | X |
| Comparative Example 5 | none | VEGFR1-fluorescent dye-containing nanoparticle | — | X | ○ |
| Comparative Example 6 | CD31-DAB | VEGFR1-fluorescent dye | same | ◉ | X |
| Comparative Example 7 | none | VEGFR1-fluorescent dye-containing nanoparticle | — | X | ○ |
| Comparative Example 8 | CD34-DAB | VEGFR1-fluorescent dye | same | ◉ | X |
| Comparative Example 9 | none | VEGFR3-fluorescent dye-containing nanoparticle | — | X | ○ |
| Comparative Example 10 | podoplanin-DAB | VEGFR3-fluorescent dye | same | ◉ | X |
| Comparative Example 11 | none | Ki67-fluorescent dye-containing nanoparticle | — | X | ○ |
| Comparative Example 12 | Cytokeratin AE1/AE3-DAB | Ki67-fluorescent dye | same | ◉ | X |
| Comparative Example 13 | none | ER-fluorescent dye-containing nanoparticle | — | X | ○ |
| Comparative Example 14 | Cytokeratin AE1/AE3-DAB | ER-fluorescent dye | same | ◉ | X |
| Comparative Example 15 | none | PgR-fluorescent dye-containing nanoparticle | — | X | ○ |

TABLE 1-2-continued

| | First immunostaining | Second immunostaining | Tissue section slide | Specification of expression positions of second biological substance (Note 1) | Determination of brightness distribution of second biological substance (Note 2) |
|---|---|---|---|---|---|
| Comparative Example 16 | Cytokeratin AE1/AE3-DAB | PgR-fluorescent dye | same | ◉ | X |
| Comparative Example 17 | none | VEGFR2-fluorescent dye-containing nanoparticle | — | X | ○ |
| Comparative Example 18 | CK7-DAB | VEGFR2-fluorescent dye | same | ◉ | X |
| Comparative Example 19 | none | VEGFR1-fluorescent dye-containing nanoparticle | — | X | ○ |
| Comparative Example 20 | CK7-DAB | VEGFR1-fluorescent dye | same | ◉ | X |
| Comparative Example 21 | none | VEGFR3-fluorescent dye-containing nanoparticle | — | X | ○ |
| Comparative Example 22 | CK7-DAB | VEGFR3-fluorescent dye | same | ◉ | X |

(Note 1) Specification of the expression positions of the second biological substance on the specific tissue or cells based on a comparison between the stained image of the first immunostaining and that of the second tissue section (the positions of bright spots and the brightness distribution on the respective fluorescently stained images of the second immunostaining):
◉: accurately and easily specifiable
○: specifiable
X: not specifiable
(Note 2) Determination of the expression amount of the second biological substance (calculation of the number of bright spots and determination of the brightness distribution on the respective fluorescently stained images of the second immunostaining):
◉: The brightness distribution could be determined and the positions of bright spots were specifiable.
○: The brightness distribution could be determined, but the positions of bright spots could not be specified.
X: The brightness distribution could not be determined.

DESCRIPTION OF SYMBOLS

1: Vascular endothelial cell
2: VEGFR2

The invention claimed is:

1. A method of quantifying a biological substance in a tissue section, said method comprising:
   (1) performing bright-field observable enzyme immunostaining that specifically stains a first biological substance in said tissue section (first immunostaining);
   (2) performing immunostaining with a fluorescent-containing nanoparticle that specifically stains a second biological substance in said tissue section (second immunostaining);
   (3) specifying the expression position(s) of said second biological substance in said tissue section by comparing the position of a stained image of said first immunostaining and position of a stained image of said second immunostaining; and
   (4) determining the expression amount of said second biological substance by measuring the fluorescence intensity of said stained image of said second immunostaining.

2. The method according to claim 1, wherein said fluorescence intensity of said stained image of said second immunostaining is measured at a position(s) where said stained image of said first immunostaining and that of said second immunostaining overlap with each other.

3. The method according to claim 1, wherein said first immunostaining and said second immunostaining are performed on the same tissue section.

4. The method according to claim 1, wherein the first biological substance comprises at least one of CD31, CD34, or podoplanin.

5. The method according to claim 1, wherein at least one of following condition (1) or (2) is satisfied:
   (1) the first biological substance comprises at least one of CD31, CD34, or podoplanin; and
   (2) the second biological substance comprises at least one of VEGFR-1, VEGFR-2, or VEGFR-3.

6. The method according to claim 1, wherein the fluorescent substance-containing nanoparticle comprises at least one of polystyrene, polyamide, polylactic acid, polyacrylonitrile, polyglycidyl methacrylate, polymelamine, polyuria, polybenzoguanamine, polyfuran, polyxylene, phenol resins, polysaccharides, or silica.

7. The method according to claim 1, wherein the second immunostaining is performed with fluorescent substance-containing nanoparticles, and an average particle size of the fluorescent substance-containing nanoparticles is 10 to 500 nm.

8. The method according to claim 7, wherein at least one of following condition (1) or (2) is satisfied:
   (1) the first biological substance comprises at least one of CD31, CD34, or podoplanin; and
   (2) the second biological substance comprises at least one of VEGFR-1, VEGFR-2, or VEGFR-3.

9. The method according to claim 7, wherein the average particle size of the fluorescent substance-containing nanoparticles is not more than 200 nm.

10. The method according to claim 7, wherein a variation coefficient in the particle size of the fluorescent substance-containing nanoparticles is 20% or less.

11. The method according to claim 10, wherein the variation coefficient is 5 to 15%.

12. The method according to claim 1, wherein the fluorescence intensity is determined based on a number of bright spots, the fluorescence brightness, or the both.

* * * * *